US006495485B2

(12) United States Patent
Hlatky et al.

(10) Patent No.: US 6,495,485 B2
(45) Date of Patent: Dec. 17, 2002

(54) SINGLE-SITE CATALYSTS BASED ON CAGED DIIMIDE LIGANDS

(75) Inventors: Gregory G. Hlatky, Morrow, OH (US); Jonathan L. Schuchardt, Royersford, PA (US)

(73) Assignee: Equistar Chemicals, LP, Houston, TX (US)

( * ) Notice: Subject to any disclaimer, the term of this patent is extended or adjusted under 35 U.S.C. 154(b) by 0 days.

(21) Appl. No.: 10/118,107

(22) Filed: Apr. 8, 2002

(65) Prior Publication Data

US 2002/0115561 A1 Aug. 22, 2002

Related U.S. Application Data

(62) Division of application No. 09/691,285, filed on Oct. 18, 2000, now Pat. No. 6,414,099.

(51) Int. Cl.$^7$ .......................... B01J 31/22; B01J 31/18; C07C 249/02
(52) U.S. Cl. ...................................... 502/167; 564/270
(58) Field of Search ........................... 502/167; 564/270

(56) References Cited

U.S. PATENT DOCUMENTS

| | | | |
|---|---|---|---|
| 4,752,597 A | 6/1988 | Turner | 502/104 |
| 4,791,180 A | 12/1988 | Turner | 526/160 |
| 5,153,157 A | 10/1992 | Hlatky et al. | 502/117 |
| 5,198,401 A | 3/1993 | Turner et al. | 502/155 |
| 5,241,025 A | 8/1993 | Hlatky et al. | 526/129 |
| 5,304,615 A | 4/1994 | Ambler et al. | 526/189 |
| 5,442,068 A | 8/1995 | Godek et al. | 546/133 |
| 5,539,124 A | 7/1996 | Etherton et al. | 548/402 |
| 5,554,775 A | 9/1996 | Krishnamurti et al. | 556/7 |
| 5,637,659 A | 6/1997 | Krishnamurti et al. | 526/133 |
| 5,637,660 A | 6/1997 | Nagy et al. | 526/160 |
| 5,714,556 A | 2/1998 | Johnson et al. | 526/135 |
| 5,731,101 A | 3/1998 | Sherif et al. | 429/102 |
| 5,827,602 A | 10/1998 | Koch et al. | 429/194 |
| 5,866,663 A | 2/1999 | Brookhart et al. | 526/170 |
| 5,892,124 A | 4/1999 | Olivier et al. | 568/374 |
| 5,902,866 A | 5/1999 | Nagy et al. | 523/133 |

OTHER PUBLICATIONS

W. Dilling, *Chem. Rev.* (1996), Intramolecular Photochemical Cycloaddition Reactions Of Nonconjugated Olefins, pp 373–393.
R. Cookson et al., *J. Chem. Soc.* (1964), Photochemical Cyclisation Of Diels—Alder Adducts, pp 3062–3075.
G. Mehta et al., *J. Org. Chem.* 56 (1991), "Roofed" Polyquinanes: Synthesis And Electronic Structure, pp 7048–7055.
G. Mehta et al., *Tetrahedron Letters,*29 (1988), A New Approach Towards Dodecahedrane. Short, Simple Design of Quinane 'Roofed' Polyquinanes, pp 5309–5312.
J. McKennis et al., *J. Am. Chem. Soc.* 93 (1971), The Degenerate Cope Rearrangements in Hypostrophene, a Novel $C_{10}H_{10}$ Hydrocarbon, pp 4957–4598.
J. March, *Advanced Organic Chemistry*, 2$^{nd}$ Ed. (1977), pp. 817–819.
J. Sauer, *Angew. Chem., Int. Ed. Engl.* 5 (1966), Diels–Alder–Reactions Part I: New Preparative Aspects, pp 211–230.
J. Sauer, *Angew. Chem., Int. Ed. Engl.* 6 (1967), Diels–Alder Reaction II: The Reaction Mechanism, pp 16–33.

*Primary Examiner*—Caixia Lu
(74) *Attorney, Agent, or Firm*—Jonathan L. Schuchardt

(57) ABSTRACT

Single-site catalysts useful for polymerizing olefins are disclosed. The organometallic catalysts incorporate a Group 3 to 10 transition, lanthanide or actinide metal and a caged diimide ligand. The diimide ligands are made by a tandem Diels-Alder and photochemical [2+2] cycloaddition sequence to give a multicyclic dione, followed by condensation with a primary amine. Because a wide variety of caged diimide ligands are easy to prepare from commercially available dienes and dienophiles, the invention enables the preparation of a new family of single-site catalysts. Based on their unique structure and geometry, the catalysts offer polyolefin producers new ways to improve activity, control comonomer incorporation, or regulate polyolefin tacticity.

4 Claims, No Drawings

SINGLE-SITE CATALYSTS BASED ON CAGED DIIMIDE LIGANDS

This is a division of Application Ser. No. 09/691,285, now U.S. Pat. No. 6,414,099 B1, filed Oct. 18, 2000.

FIELD OF THE INVENTION

The invention relates to catalysts useful for polymerizing olefins. In particular, the invention relates to catalysts that contain diimide ligands having multiple carbocyclic rings and a cage-like structure ("caged diimide ligands.") The caged diimides are particularly valuable for use with late transition metal catalysts.

BACKGROUND OF THE INVENTION

Interest in single-site (metallocene and non-metallocene) catalysts continues to grow rapidly in the polyolefin industry. These catalysts are more reactive than Ziegler-Natta catalysts, and they produce polymers with improved physical properties. The improved properties include narrow molecular weight distribution, reduced low molecular weight extractables, enhanced incorporation of α-olefin comonomers, lower polymer density, controlled content and distribution of long-chain branching, and modified melt rheology and relaxation characteristics.

Traditional metallocenes commonly include one or more cyclopentadienyl groups, but many other ligands have been used. Putting substituents on the cyclopentadienyl ring, for example, changes the geometry and electronic character of the active site. Thus, a catalyst structure can be fine-tuned to give polymers with desirable properties. Other known single-site catalysts replace cyclopentadienyl groups with one or more heteroatomic ring ligands such as boraaryl (see, e.g., U.S. Pat. No. 5,554,775), pyrrolyl, indolyl, (U.S. Pat. No. 5,539,124), or azaborolinyl groups (U.S. Pat. No. 5,902,866).

Single-site catalysts based on "late" transition metals (especially those in Groups 8–10, such as Fe, Ni, Pd, and Co) and diimines or other ligands have recently sparked considerable research activity because of the unusual ability of these catalysts to incorporate functionalized comonomers or to give branched polyethylenes without including a comonomer. See, for example, U.S. Pat. Nos. 5,714,556 and 5,866,663 and PCT international applications WO 96/23010, WO 98/47933, and WO 99/32226. These catalysts are often less active than would otherwise be desirable.

The diimine ligands described above are often called "Brookhart" ligands or "Brookhart-DuPont" ligands because much of the early work in this area was performed by Professor Maurice Brookhart (University of North Carolina at Chapel Hill) and scientists at E.I. du Pont de Nemours and Company (Wilmington, Del.). The vast majority of Brookhart ligands used to date are α-diimines, i.e., they derive from 1,2-diketones (as indicated by the "DAB" acronym used in the references to identify the 1,4-diaza-1,3-butadiene structural subunit). Other diimines derived from alkylene diamines (e.g., 1,3-propanediamine) and simple aldehydes or ketones are also taught (see, e.g., U.S. Pat. No. 5,866,663, formula (XXX), column 3, where n=2 or 3). Diimines derived from primary amines and multicyclic diketones are generally unknown as ligands for olefin polymerization catalysts.

The Diels-Alder reaction is legendary in synthetic organic chemistry because of its phenomenal utility for creating complex carbocyclic compounds with predictable stereospecificity. Simple heating of dienes and dienophiles gives a wide variety of substituted cyclohexenes in a [4+2] cycloaddition reaction. Another synthetically valuable reaction involves the photochemical [2+2] cycloaddition reaction, which converts two proximally oriented olefin groups into a cyclobutane ring. This transformation is accomplished by irradiating two olefins (usually a diolefin) with light of a suitable energy under reaction conditions that favor cyclization. By performing a Diels-Alder reaction in tandem with a photochemical [2+2] cycloaddition, one can create remarkably complex, multicyclic compounds from readily available dienes and dienophiles in two simple steps (see, e.g., G. Mehta, *Tetrahedron* 37 (1981) 4543). In spite of the availability of the Diels-Alder reaction and photochemical cycloadditions, these reactions have not been exploited to prepare ligands useful for single-site olefin polymerization catalysts.

In sum, there is a continuing need for new ligands and new single-site catalysts for olefin polymerization processes. In particular, there is a need for ligands that can be used with late transition metals to boost activity, improve catalyst solubility, and facilitate polar comonomer incorporation. Ideally, the ligands and catalysts could be made easily from readily available starting materials.

SUMMARY OF THE INVENTION

The invention is catalyst system useful for polymerizing olefins. The catalyst system comprises an organometallic complex and an optional activator. The complex includes a Group 3 to 10 transition, lanthanide or actinide metal and a caged diimide ligand. In a preferred catalyst system of the invention, the catalyst incorporates a "late" transition metal, i.e., a metal from Groups 6 to 8. The invention includes caged diimide ligands prepared by a tandem Diels-Alder and photochemical [2+2] cycloaddition sequence to give a multicyclic dione, followed by condensation with a primary amine. Because a wide variety of caged diimide ligands are easy to prepare from commercially available dienes and dienophiles, the invention enables the preparation of a new family of single-site catalysts. Based on their unique structure and geometry, the catalysts offer polyolefin producers new ways to improve activity, control comonomer incorporation, or regulate polyolefin tacticity.

DETAILED DESCRIPTION OF THE INVENTION

Catalyst systems of the invention comprise an organometallic complex and an optional activator. The complex is "single site" in nature, i.e., it is a distinct chemical species rather than a mixture of different species. Single-site catalysts, which include metallocenes, typically give polyolefins with characteristically narrow molecular weight distributions (Mw/Mn<3) and good, uniform comonomer incorporation.

The organometallic complex includes a Group 3 to 10 transition metal or lanthanide or actinide metal, M. More preferred complexes include a Group 4 to 8 transition metal. Particularly preferred complexes incorporate a "late" transition metal, i.e., a metal from Groups 6 to 8, i.e., chromium, manganese, iron, cobalt, nickel, and elements directly below these on the Periodic Table.

The complex includes a caged diimide ligand. "Caged" means that the ligand has a multicyclic structure that surrounds the imide groups and resembles a cage or container. "Cage compounds" are a well-known class of carbocyclic materials of interest to synthetic organic chemists. They include adamantanes, cubanes, polyquinanes, fullerenes (e.g., "Buckyballs"), and other interesting groups of compounds.

The caged diimide ligand typically features multiple five or six-membered rings. Preferred ligands are "diquinanes." As used herein, "diquinane" refers to carbocyclic compounds that have at least two nonfused five-membered rings that share at least two carbon-carbon bonds and are oriented such that the five-membered rings occupy opposite "faces" in the structure, similar to the way in which the two-dotted and five-dotted sides occupy opposite faces on a six-sided die.

The caged ligand is a "diimide," i.e., it is a diimine condensation product of a diketone and two equivalents of a primary amine or ammonia. Each imine has the general structure $R_2C=NR'$ in which C and each R are part of one of a five or six-membered ring, and R' is preferably hydrogen or a $C_1$–$C_{30}$ alkyl, aryl, or aralkyl group.

Caged diimides useful as ligands for catalyst systems of the invention can be made by any desired method. One particularly valuable method involves the use of tandem Diels-Alder and photochemical [2+2] cycloaddition reactions starting with a diquinone, preferably p-benzoquinone or a halogenated p-benzoquinone such as 2,3,5,6-tetrachloro-p-benzoquinone. The resulting multicyclic dione is then reacted with two equivalents of ammonia or a primary amine to give the caged diimide ligand. The only required reactants are a diene, a dienophile, and the amine. First, a diene and a dienophile are heated, optionally in the presence of an inert solvent, to produce a Diels-Alder adduct that contains two proximal carbon-carbon double bonds (see, e.g., Scheme 1) or one carbon-carbon double bond and one cyclopropane ring (Scheme 2). This reaction usually takes place at elevated temperature, optionally in the presence of a solvent, and preferably at a temperature within the range of about 80° C. to about 300° C. Suitable procedures are described in Wasserman, *Diels-Alder Reactions*, American Elsevier Publishing Co., Inc. (1965), in Sauer, *Ang. Chem. Int. Ed. Engl.*, 5 (1966) 211–230 (1966) and 6 (1967) 16–33, and references cited therein.

The Diels-Alder adduct is then irradiated with light of a selected energy to cause a [2+2] cycloaddition reaction. Steric crowding or locked-in geometry in the Diels-Alder adduct forces the reacting bonds into close proximity. When the adduct contains two carbon-carbon double bonds, the resulting [2+2] cycloaddition product is a diketone that contains a cyclobutane ring (see Scheme 1). On the other hand, when the Diels-Alder adduct contains one carbon-carbon double bond and a cyclopropane ring (i.e., when a bicyclic diene is used) the resulting diketone contains an additional cyclopentane ring (see Scheme 2).

Scheme 1
Preparation of Caged Diketones
from Monocyclic or Hindered Acyclic Dienes

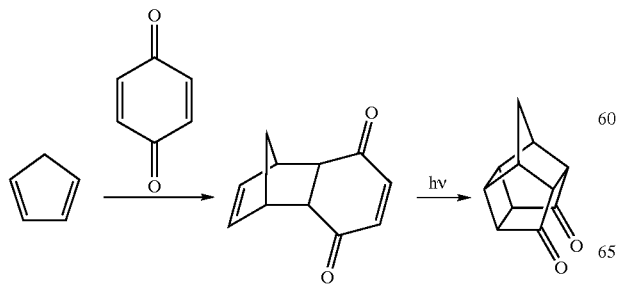

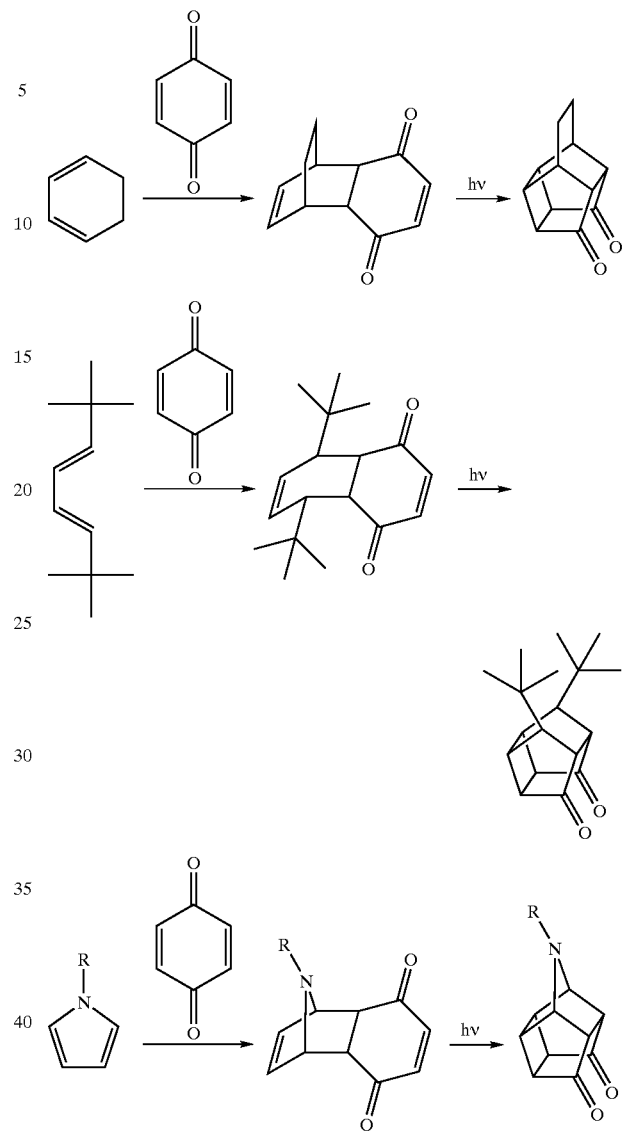

Scheme 2
Preparation of Caged Diketones from Bicyclic Dienes

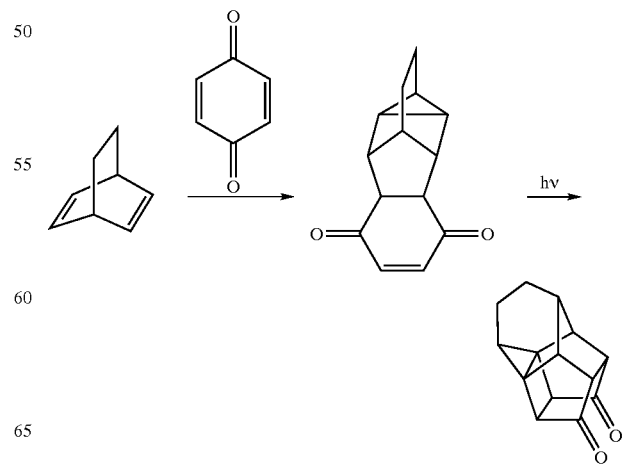

-continued

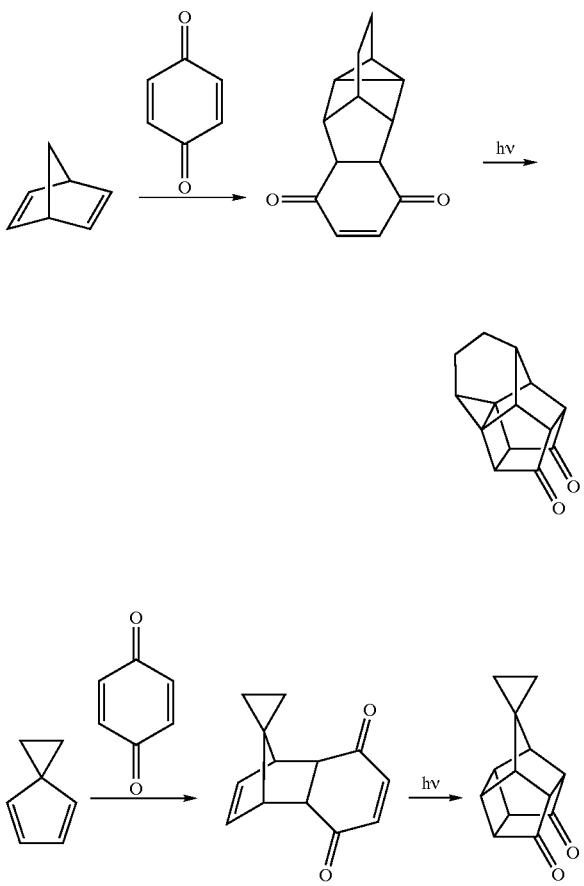

The schemes above merely show a few examples of the kinds of skeletons possible for caged diimide ligands. Others are shown, for example, in G. Mehta et al., *J. Org. Chem.* 56 (1991) 7048 and R. Cookson et al., *J. Chem. Soc.* (1964) 3062. Additional suitable procedures for effecting the photochemical [2+2] cycloadditions appear in A. Schonberg, *Preparative Organic Photochemistry* (1968), D. Cowan and R. Drisko, *Elements of Organic Photochemistry* (1976), and references cited therein. Obviously, the diene, the dienophile, or both, can be substituted with groups that are reasonably inert to both the thermal Diels-Alder reaction and the photochemical cycloaddition (see, for example, Scheme 3, below). Suitable substituents include, for example, halide, alkyl, aryl, aralkyl, alkoxy, trialkylsilyl, cyano, or the like.

When reacted with benzoquinones, cyclic dienes, such as cyclopentadiene or cyclohexa-1,3-diene, and bicyclic dienes, such as bicyclo[2.2.1]hepta-2,5-diene or bicyclo[2.2.2]octa-2,5-diene, give Diels-Alder adducts that are well oriented to undergo the desired [2+2] cycloaddition upon photolysis. When an acyclic diene is used, it preferably has bulky substituents on the 1 and 4 carbons of the diene, such as tert-butyl, isopropyl, or other branched hydrocarbyl groups. Steric crowding of these groups encourages a conformation that favors the intramolecular [2+2] cycloaddition in the next step. Thus, preferred acyclic dienes include 1,4-di-tert-butyl-1,3-butadiene, 1,4-diisopropyl-1,3-butadiene, 1,4-dicyclohexyl-1,3-butadiene, and the like. On the other hand, unsubstituted dienes are generally not suitable; photolysis of the Diels-Alder adduct from 1,3-butadiene and p-benzoquinone, for example, gives a dimer or tar instead of an intramolecular cycloaddition product (Cookson et al., *J. Chem. Soc.* (1964) at 3064).

The caged diketones prepared as described above are easily converted to diimides by condensing them with two equivalents of a primary amine or ammonia. As noted earlier, each imine has the general structure $R_2C=NR'$ in which C and each R are part of a five or six-membered ring, and R' is preferably hydrogen or a $C_1$–$C_{30}$ alkyl, aryl, or aralkyl group. Amines suitable for use are ammonia and primary amines $R'NH_2$ in which R' is a $C_1$–$C_{30}$ alkyl, aryl, or aralkyl group. Particularly preferred amines are methylamine, ethylamine, isobutylamine, aniline, toluidine, and the like.

In a particularly preferred example, the diimide is obtained from the reaction of readily available p-benzoquinone and cyclopentadiene (see the first example in Scheme 1). The resulting pentacyclic diketone is converted to a diimide ligand with two equivalents of a primary amine, preferably an aromatic amine such as aniline:

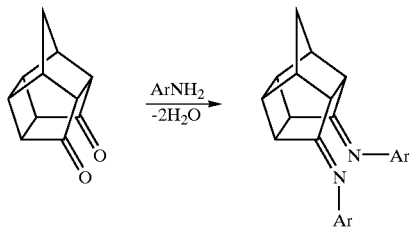

The condensation reaction used to produce the diimine is the well-known "Schiff base" reaction (see J. March, *Advanced Organic Chemistry*, 2d ed. (1977), p. 817 and references cited therein). In preparing imines from hindered ketones such as the caged diketones described herein, it is preferable to react the amine and ketone at elevated temperature and to remove water as the reaction proceeds. In one suitable method, the reactants are heated in the presence of a sulfonic acid and an aromatic hydrocarbon solvent (e.g., toluene), and water is removed as it forms using a Dean-Stark distillation setup. U.S. Pat. No. 5,442,068, the teachings of which are incorporated herein by reference, shows an example of this technique in reacting a hindered, bicyclic ketone with 2-methoxybenzylamine in the presence of toluene and camphorsulfonic acid to produce the desired imine (see Example 1 of the '068 patent).

As those skilled in the art will appreciate, there are many synthetic routes to caged diketones that are precursors to the caged diimides described herein. Many of these routes employ Diels-Alder chemistry, photochemical cycloadditions, or both. While caged diquinane systems such as those described in Schemes 1 and 2 are preferred, ligands used to make catalyst systems of the invention are not limited to diquinanes. Suitable six-ring systems are available, for example, from the reaction of a cyclic diene and cycloocta-2,6-dien-1,4-dione as shown below:

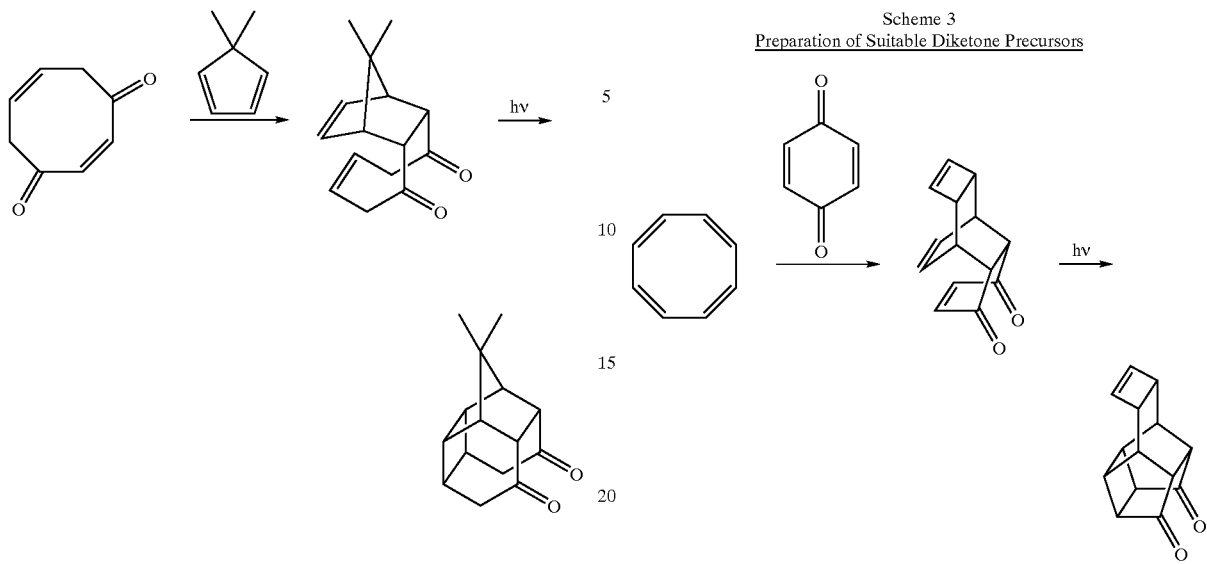

Another suitable diketone precursor is obtained by thermal reaction of 1,3,5,7-cyclooctatetraene with a quinone followed by photolysis according to Cookson's procedure (*J. Chem. Soc.* (1964) 3062). Cookson also shows how to use halogenated dienes or dienophiles (see Scheme 3 below).

The Diels-Alder adduct from benzo-p-benzoquinone or its saturated analog and cyclopentadienes can also be used as the starting point for making caged diketones with the now-familiar photolytic [2+2] cycloaddition as the second step, as shown in Scheme 4 and as described in *Tetrahedron Letters* (1971) 3275.

Suitable diquinane diketones can also be made by reacting benzoquinones with transition metal complexes of cyclobutadiene as shown by R. Pettit et al. (*J. Am. Chem. Soc.* 93 (1971) 4957):

Scheme 3
Preparation of Suitable Diketone Precursors

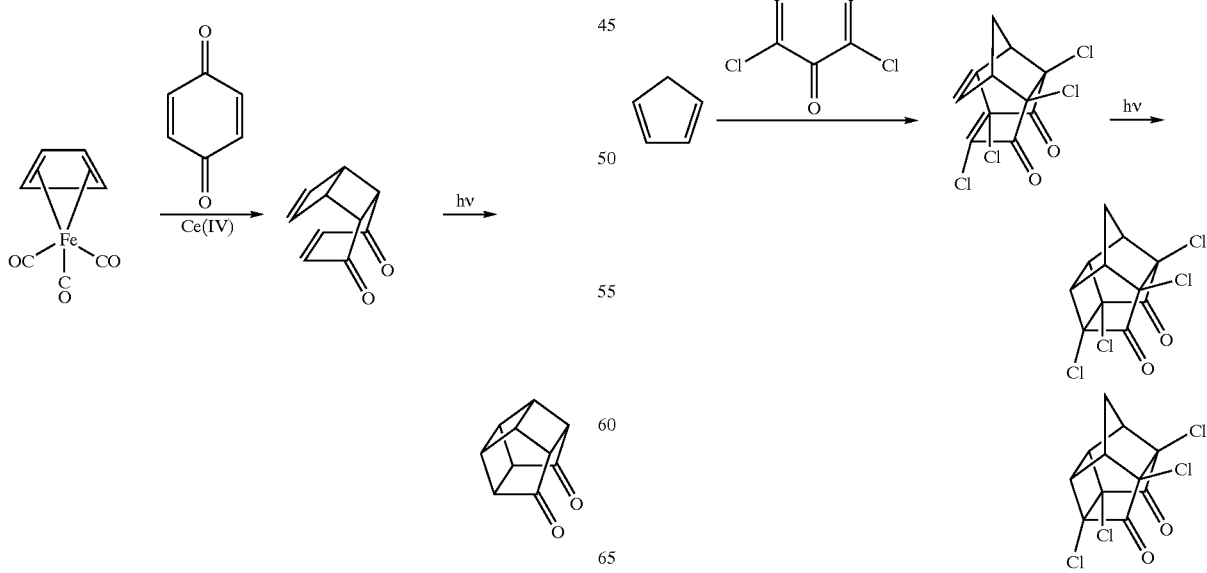

Scheme 4
Suitable Diketone Precursors

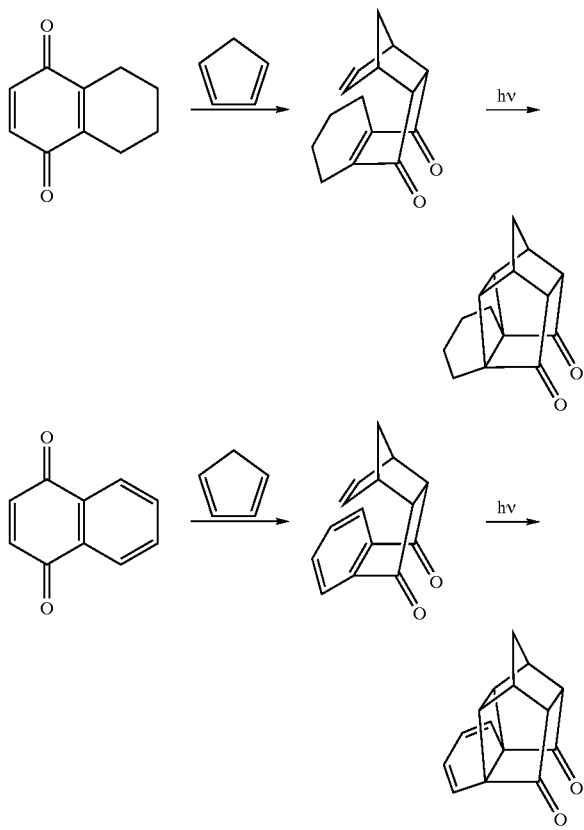

Additional routes to caged diketone precursors have been described. Some of these are summarized by W. Dilling (*Chem. Rev.* (1966) 373, especially Schemes IX, XXII, XXIII, and XXIV in this reference).

In addition to a caged diimide ligand, the organometallic complex may include additional labile or polymerization-stable, anionic ligands. Polymerization-stable ligands include, for example, substituted and unsubstituted cyclopentadienyl, fluorenyl, and indenyl, or the like, such as those described in U.S. Pat. Nos. 4,791,180 and 4,752,597, the teachings of which are incorporated herein by reference. Suitable polymerization-stable ligands include heteroatomic ligands such as boraaryl, pyrrolyl, indolyl, quinolinyl, pyridinyl, and azaborolinyl as described in U.S. Pat. Nos. 5,554,775, 5,539,124, 5,637,660, and 5,902,866, the teachings of which are incorporated herein by reference. Suitable polymerization-stable ligands include indenoindolyl anions such as those described in PCT publication WO 99/24446. The organometallic complex usually includes one or more labile ligands such as halides, alkyls, alkaryls, aryls, dialkylaminos, or the like. Particularly preferred are halides, alkyls, and alkaryls (e.g., chloride, methyl, benzyl). A variety of other kinds of ligands are particularly useful with late transition metals, including, for example, N,N'-diaryl-substituted diazabutanes and other imines as described in U.S. Pat. Nos. 5,714,556 and 5,866,663, the teachings of which are incorporated herein by reference. The organometallic complex can include up to two caged diquinane diimide ligands.

The catalyst system optionally includes an activator. Suitable activators help to ionize the organometallic complex and activate the catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis (pentafluorophenyl)borate, lithium tetrakis(pentafluorophenyl)aluminate, anilinium tetrakis(pentafluorophenyl) borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153,157, 5,198,401, and 5,241,025, the teachings of which are incorporated herein by reference.

The optimum amount of activator needed relative to the amount of organometallic complex depends on many factors, including the nature of the complex and activator, whether a supported catalyst is used, the desired reaction rate, the kind of polyolefin product, the reaction conditions, and other factors. Generally, however, when the activator is an alumoxane or an alkyl aluminum compound, the amount used will be within the range of about 0.01 to about 5000 moles, preferably from about 0.1 to about 500 moles, of aluminum per mole of transition, lanthanide, or actinide metal, M. When the activator is an organoborane or an ionic borate or aluminate, the amount used will be within the range of about 0.01 to about 5000 moles, preferably from about 0.1 to about 500 moles, of activator per mole of M.

The activator is normally added to the reaction mixture at the start of the polymerization. However, when a supported catalyst system is used, the activator can be deposited onto the support along with the organometallic complex.

The organometallic complex is prepared according to methods that are well known in the art. In general, the complexes are made by combining the diimide with a transition metal source. Any convenient source of transition metal can be used. For example, the complexes can be made from transition metal halides, alkyls, alkoxides, acetates, amides, or the like. A particularly convenient source of the transition metal is the transition metal halide. For example, one can use vanadium(III)chloride-tetrahydrofuran complex (VCl$_3$(THF)$_3$), titanium (III)chloride THF complex, chromium(III)chloride-THF complex, cobalt(II) chloride, nickel(II) bromide, platinum(II)chloride, palladium(II) chloride, lanthanum(II) chloride, titanium(III)acetate, or the like. Complexes can also be prepared from salts with labile groups, such as tetrakis(acetonitrile)palladium(II) bis (tetrafluoroborate).

The transition metal complexes are easy to make. Usually, the transition metal source (halide, e.g.) is dissolved or suspended in an organic solvent and the caged diimide ligand is carefully added. Refluxing is used if needed to complete the reaction. Insoluble by-products, if any, can be removed by filtration, solvents are evaporated, and the transition metal complex is isolated, washed, and dried. The resulting complex can generally be used without further purification.

The organometallic complexes of the invention are expected to be valuable catalysts, catalyst precursors, or reagents for a variety of organic reactions, including, for example, olefin metathesis, isomerization, oligomerization, and polymerization reactions.

The catalyst systems are optionally used with an inorganic solid or organic polymer support. Suitable supports include silica, alumina, silica-aluminas, magnesia, titania, clays, zeolites, or the like. The supports can be pretreated thermally or chemically to improve catalyst productivity or product properties. The catalysts can be deposited on the support in any desired manner. For instance, the catalyst can be dissolved in a solvent, combined with a support, and stripped. Alternatively, an incipient-wetness technique can be used. Moreover, the support can simply be introduced into the reactor separately from the catalyst. The caged diimide ligand can also be chemically tethered to the support through a suitable linking group.

The invention includes an olefin polymerization process. The process comprises polymerizing an olefin in the presence of a catalyst system of the invention according to methods that are well known in the art. Olefins useful in the process of the invention are compounds having at least one polymerizable carbon-carbon double bond. Preferred olefins have a single carbon-carbon double bond. They include ethylene and $C_3$–$C_{20}$ α-olefins such as propylene, 1-butene, 1-hexene, 1-octene, and the like. Isoolefins (e.g., isobutene or isooctene) or cycloolefins (e.g., cyclohexene) are suitable as are cyclic olefins (e.g., norbornene) and dienes (e.g., 1,3-butadiene). Some or all of the olefin can be replaced with an acetylenically unsaturated monomer (e.g., 1-octyne or 1-hexyne). Mixtures of olefins can be used. Ethylene and mixtures of ethylene with $C_3$–$C_{10}$ α-olefins are especially preferred.

Functionalized comomoners can be included provided that the comonomer also contains at least one polymerizable carbon-carbon double bond. Such functionalized monomers are used advantageously with late transition metal catalysts. For example, the olefin polymerization can be conducted in the presence of a minor proportion of allyl alcohol, acrylic acid, hydroxyethylmethacrylate, or the like. Olefin polymers prepared by the process of the invention have recurring olefin units.

Alternating copolymers of ethylene or other α-olefins, diolefins, or cyclic olefins with carbon monoxide or sulfur dioxide are also accessible using catalysts of this invention. Catalysts of the later transition metals (iron, cobalt, and nickel triads) are particularly useful for copolymerizing these monomers.

The polymerization is advantageously performed in the presence of an ionic liquid. Copending U.S. application Ser. No. 09/557,429, filed Apr. 25, 2000, the teachings of which are incorporated herein by reference, explains how to use ionic liquids with single-site catalyzed olefin polymerizations. Suitable ionic liquids are salts that exist in the liquid state at temperatures used to polymerize olefins. Preferred ionic liquids are liquids at and below room temperature, and many are liquids at temperatures as low as about −100° C. Preferably, the ionic liquids consist of a bulky organic cation and a non-coordinating, complex inorganic anion. The anion is "non-interfering" with respect to the single-site catalyst, i.e., it does not prevent or significantly inhibit the catalyst from effecting polymerization of the olefin. A wide variety of ionic liquids suitable for use in the process of the invention have been described. For example, U.S. Pat. Nos. 5,827,602, 5,731,101, 5,304,615, and 5,892,124, the teachings of which are incorporated herein by reference, disclose many suitable ionic liquids.

Many types of olefin polymerization processes can be used. Preferably, the process is practiced in the liquid phase, which can include slurry, solution, suspension, or bulk processes, or a combination of these. High-pressure fluid phase or gas phase techniques can also be used. The process of the invention is particularly valuable for solution and slurry processes. Suitable methods for polymerizing olefins using the catalysts of the invention are described, for example, in U.S. Pat. Nos. 5,902,866, 5,637,659, and 5,539,124, the teachings of which are incorporated herein by reference.

The following examples merely illustrate the invention. Those skilled in the art will recognize many variations that are within the spirit of the invention and scope of the claims.

EXAMPLE 1

Tandem Diels-Alder and Photochemical Cycloadditions

Preparation of a Caged, Diquinane Diketone

The procedure of Cookson et al. (*J. Chem. Soc.* (1964) at 3071) is followed to produce a caged diketone. The Diels-Alder adduct of cyclopentadiene and p-benzoquinone (19 g), produced as reported by Diels et al., *Annalen,* 443 (1925) 247, is dissolved in ethyl acetate (300 mL) and the mixture is irradiated for 6 h using Cookson's method. The resulting colorless solution is evaporated under reduced pressure to give a crystalline product. This material is collected, washed, and sublimed to give the expected caged diketone, which is also known as pentacyclo[$5.4.0^{2.6}.0^{3.10}.0^{5.9}$] undecane-8,11-dione (see Scheme 1 above, first example) and is commercially available from Aldrich Chemical Company.

EXAMPLE 2

Preparation of a Caged, Diquinane Diimine

A portion of the caged diketone obtained in Example 1 (1.0 g, 5.7 mmol) is dissolved in toluene (20 mL). Aniline (2.2 eq, 1.18 g, 12.6 mmol) is added, along with p-toluenesulfonic acid (10 mg). The mixture is heated to reflux (115° C.) for 4 days, and water of reaction is removed using a Dean-Stark trap. When the reaction is complete, the toluene is removed in vacuo, and the resulting diimine product is purified by recrystallization from petroleum ether.

EXAMPLE 3

Preparation of Cobalt Diimide Complex (I)

Cobalt (II) chloride (0.37 g, 2.85 mmol) and half of the diimine product of Example 2 (0.93 g, 2.85 mmol) are refluxed in THF (15 mL) for 1 h. The solvent is evaporated, and the solids are collected with pentane. The dichlorocobalt diimide addition product (I) is the expected complex:

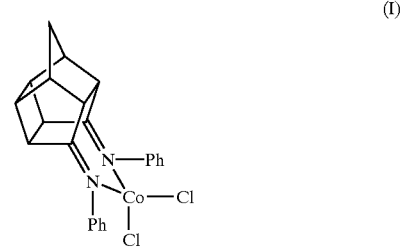

(I)

EXAMPLE 4

Preparation of Nickel Diimide Complex (II)

Nickel (II) bromide (0.62 g, 2.85 mmol) is suspended in THF (15 mL). Half of the diimine product of Example 2

(0.93 g, 2.85 mmol) is added, and the mixture is refluxed for 1.5 h and is filtered. The filtrate is evaporated, and the solids are collected with pentane, filtered, and dried. The dibromonickel diimide addition product (II) is the expected complex:

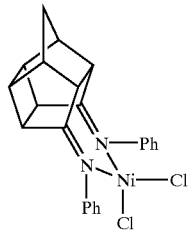

(II)

EXAMPLE 5

Polyethylene Preparation Using Nickel Diimide Complex (II)

Methyl alumoxane (5 mL of 10 wt. % MAO in toluene) is added to the product of Example 4 (200 mg). The mixture is injected into a 1.7 L stainless-steel autoclave containing dry, deoxygenated isobutane (850 mL) and triisobutylaluminum (0.2 mmol). The autoclave is heated to 80° C. and is pressurized with ethylene (150 psi). After 1 h, the autoclave is cooled, isobutane is flashed off, and polyethylene, the expected product, is isolated.

The preceding examples are meant only as illustrations. The following claims define the invention.

We claim:

1. A caged diimine prepared by:

(a) heating a diene with a benzoquinone to form a Diels-Alder adduct;

(b) photolyzing the product from step (a) to form a caged dione [2+2] cycloaddition product; and (c) condensing the caged dione with a primary amine.

2. The diimine of claim 1 wherein the diene is selected from the group consisting of cyclopentadiene, hexachlorocyclopentadiene, cyclohexa-1,3-diene, bicyclo[2.2.1]hepta-2,5-diene, and bicyclo[2.2.2]octa-2,5-diene.

3. The diimine of claim 1 wherein the benzoquinone is selected from the group consisting of p-benzoquinone, benzo-p-benzoquinone, and 2,3,5,6-tetrachlorobenzoquinone.

4. The diimine of claim 1 wherein the primary amine is aromatic.

* * * * *

UNITED STATES PATENT AND TRADEMARK OFFICE
CERTIFICATE OF CORRECTION

PATENT NO. : 6,495,485 B2
DATED : December 17, 2002
INVENTOR(S) : Gregory G. Hlatky et al.

It is certified that error appears in the above-identified patent and that said Letters Patent is hereby corrected as shown below:

Column 4,
Line 63,

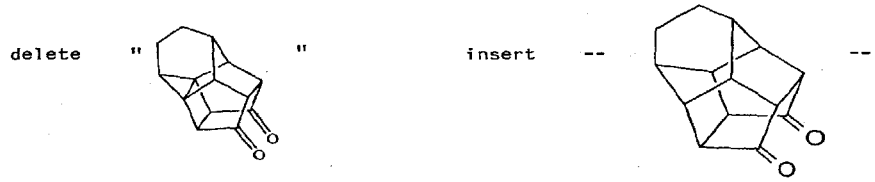

Column 5,
Line 8,

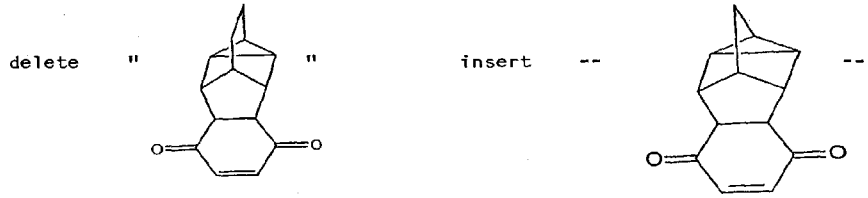

Line 18,

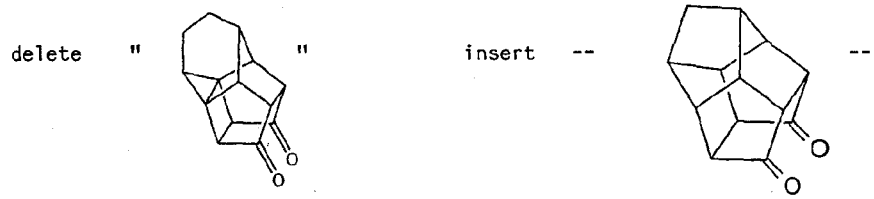

Signed and Sealed this

Fifteenth Day of April, 2003

JAMES E. ROGAN
*Director of the United States Patent and Trademark Office*